(12) United States Patent
Adhyaru

(10) Patent No.: US 11,439,803 B2
(45) Date of Patent: Sep. 13, 2022

(54) MEDICANT APPLICATOR

(71) Applicant: Niva Medtech LLC, Bullard, TX (US)

(72) Inventor: Harsh Yogeshkumar Adhyaru, Bullard, TX (US)

(73) Assignee: NIVA MEDTECH LLC, Bullard, TX (US)

(*) Notice: Subject to any disclaimer, the term of this patent is extended or adjusted under 35 U.S.C. 154(b) by 77 days.

(21) Appl. No.: 16/779,277

(22) Filed: Jan. 31, 2020

(65) Prior Publication Data

US 2020/0246600 A1 Aug. 6, 2020

Related U.S. Application Data

(60) Provisional application No. 62/799,223, filed on Jan. 31, 2019.

(51) Int. Cl.
*A61M 31/00* (2006.01)

(52) U.S. Cl.
CPC ..... *A61M 31/007* (2013.01); *A61M 2205/582* (2013.01); *A61M 2205/583* (2013.01)

(58) Field of Classification Search
CPC ...... A61M 31/007; A61M 3/00; A61M 5/178; A61M 5/3137; A61M 5/31511; A61M 2005/31518; A61M 5/31576; A61M 5/502; A61M 2005/5033; A61M 5/5086; A61M 2205/583; A61M 2205/582; A61M 2025/0008

See application file for complete search history.

(56) References Cited

U.S. PATENT DOCUMENTS

| | | | | |
|---|---|---|---|---|
| 1,538,678 A | * | 5/1925 | Blinn | A61M 31/007 604/59 |
| 1,538,679 A | * | 5/1925 | Blinn | A61M 31/007 604/59 |
| 2,754,822 A | * | 7/1956 | Emelock | A61M 31/007 604/59 |
| 3,297,031 A | * | 1/1967 | Bray | A61M 31/007 604/59 |
| 3,347,234 A | * | 10/1967 | Voss | A61F 13/26 604/14 |

(Continued)

FOREIGN PATENT DOCUMENTS

| | | |
|---|---|---|
| CN | 201379893 Y | 1/2010 |
| CN | 204121588 U | 1/2015 |
| WO | WO2017035335 A1 | 3/2017 |

*Primary Examiner* — Nilay J Shah

(57) ABSTRACT

A medicant dispenser enabling the effective administration of tableted pharmaceutical products within a body cavity has a plunger, a barrel, and a deformable tip. The deformable tip provides a suitable leading element to allow the barrel to enter the body cavity, wherein the plunger may be pushed to eject the tableted pharmaceutical products into the body cavity through the deformable tip. More specifically, the deformable tip will comprise a plurality of cuspids fixed to a support ring, wherein the support ring is fitted to a terminal end of the barrel. The plurality of cuspids will collapse concentrically to form a tapered leading element of the medicant applicator while retaining the capacity to separate to allow passage of the tableted pharmaceutical products and a head of the plunger therethrough.

13 Claims, 4 Drawing Sheets

(56) References Cited

U.S. PATENT DOCUMENTS

| | | | |
|---|---|---|---|
| 3,830,236 A * | 8/1974 | Hanke | A61F 13/26 |
| | | | 604/14 |
| 4,011,868 A * | 3/1977 | Friend | A61M 5/31511 |
| | | | 604/194 |
| 4,581,023 A * | 4/1986 | Kuntz | A61M 5/24 |
| | | | 604/234 |
| 5,067,948 A * | 11/1991 | Haber | A61M 5/2448 |
| | | | 604/213 |
| 5,578,015 A * | 11/1996 | Robb | A61M 5/315 |
| | | | 604/110 |
| 5,611,778 A * | 3/1997 | Brinon | A61M 25/01 |
| | | | 604/117 |
| 6,206,867 B1 | 3/2001 | Osborn, III et al. | |
| 7,172,573 B1 | 2/2007 | Lamb | |
| 7,591,808 B2 | 9/2009 | DiPiano et al. | |
| 2004/0092906 A1 | 5/2004 | Tosato | |
| 2007/0270763 A1* | 11/2007 | Tanner | A61M 5/50 |
| | | | 604/232 |
| 2010/0010471 A1* | 1/2010 | Ladd | A61M 31/007 |
| | | | 604/514 |
| 2010/0179507 A1* | 7/2010 | Hess | A61B 17/8833 |
| | | | 604/500 |

* cited by examiner

MEDICANT APPLICATOR

The current application claims a priority to the U.S. Provisional Patent application Ser. No. 62/799,223 filed on Jan. 31, 2019.

FIELD OF THE INVENTION

The present invention relates generally to specialized medical tools and equipment. More specifically, the present invention relates to a specialized tool suitable for the rapid insertion of medicant tablets into a body cavity.

BACKGROUND OF THE INVENTION

Obstetricians and new mothers alike know that childbirth is an arduous and tiring task. To preserve the wellbeing of both the mother and the child a doctor may need to induce labor, accelerating the process of an otherwise spontaneous labor to shorten the process of childbirth. A common method for induction of labor is the vaginal administration misoprostol tablet(s), intended to facilitate rapid cervical ripening and stimulate uterine contractions. Additionally, misoprostol may be administered rectally at higher doses to treat postpartum hemorrhage. However, current means of inserting the misoprostol tablet into the vagina are recognized to have significant drawbacks. During vaginal application a physician must manually push the medicant tablets all the way up to the posterior fornix, requiring that at least two fingers are inserted deep into the vagina. Further, the tablet may be broken, dislodged, or crushed between the fingers during insertion by this method. For rectal administration, a similar manual procedure is simply too slow to be effective during an emergency such as postpartum hemorrhage. The higher required dosage means that a physician must manually insert roughly three to ten individual tablets in rapid succession, causing significant discomfort to an already distressed patient. It is therefore recognized that a tool suitable for rapid, precise placement of misoprostol tablets in a body cavity with a minimum of patient discomfort is desirable.

The present invention provides a versatile, low-cost solution to the shortcomings of manual administration of misoprostol in an obstetric context. Further, is anticipated that the present invention as described herein may be suitable for the targeted application of any tableted medicant compound as may be realized by an individual of reasonable skill. In addition to a sterile insertable body, the present invention features specific structures that enhance the user experience for both physician and patient. More specifically, ergonomic features of the present invention enable a user to effectively direct the dispensation of medicant while simultaneously providing tactile and auditory feedback to said user regarding the volume of medicant dispensed. It is further considered that the specific shape and structure of the patient-proximal formation of the present invention will both provide a maximum of comfort during insertion while simultaneously enabling effective ejection of medicant on-demand.

DETAIL DESCRIPTIONS OF THE INVENTION

All illustrations of the drawings are for the purpose of describing selected versions of the present invention and are not intended to limit the scope of the present invention.

In reference to FIG. 1 through 4, the present invention is a medicant applicator. The medicant applicator provides a versatile, low-cost solution to the shortcomings of manual administration of misoprostol in an obstetric context. Further, it is anticipated that the medicant applicator as described herein may be suitable for the targeted application of any tableted medicant compound as may be realized by an individual of reasonable skill. In addition to a sterile insertable body, the medicant applicator features specific structures that enhance the user experience for both physician and patient. More specifically, ergonomic features of the medicant applicator enable a user to effectively direct the dispensation of medicant while simultaneously providing tactile and auditory feedback to said user regarding the volume of medicant dispensed. It is further considered that the specific shape and structure of the patient-proximal formation of the medicant applicator will both provide a maximum of comfort during insertion while simultaneously enabling effective ejection of medicant on-demand.

Figure 1:
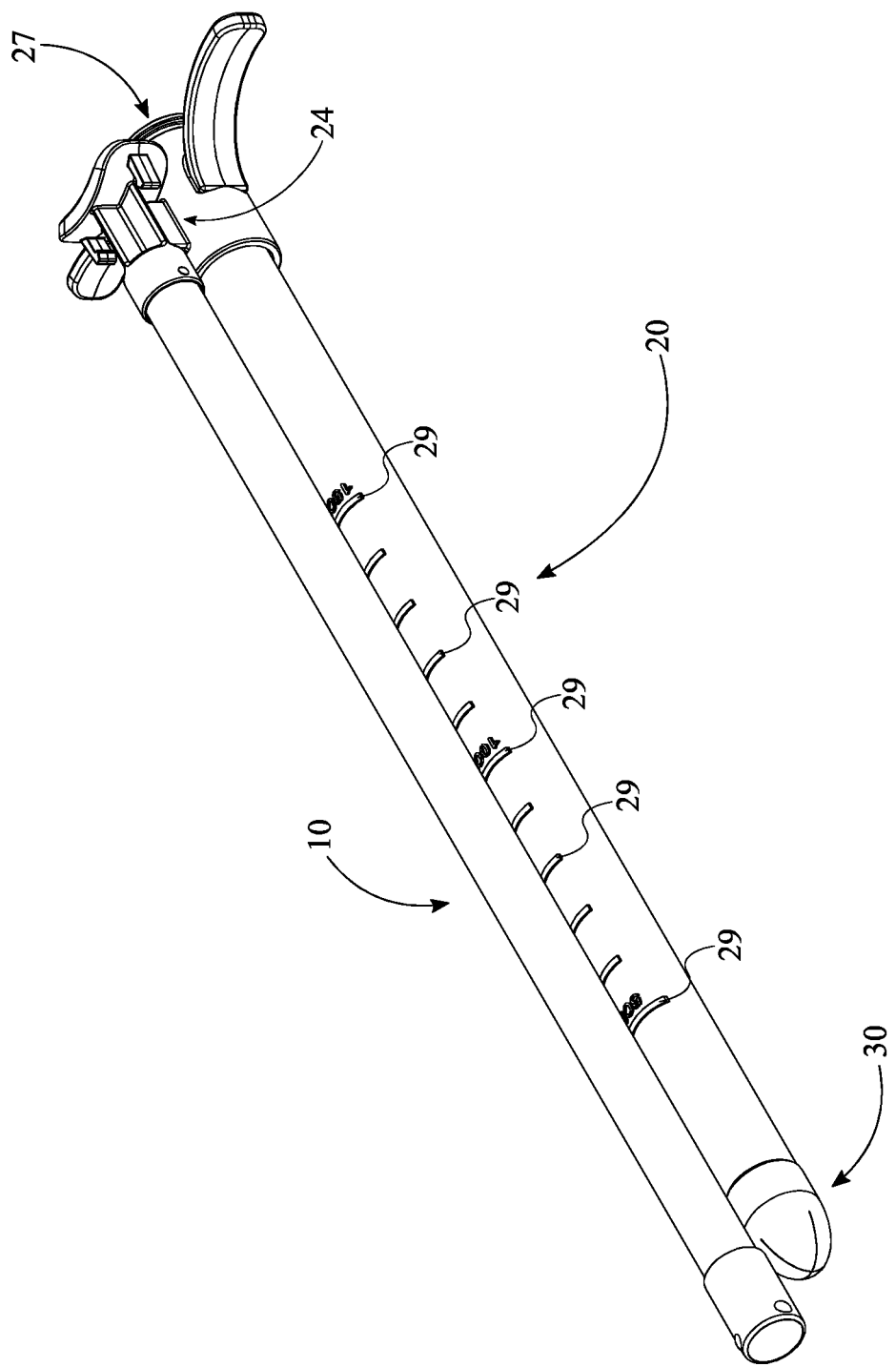
FIG. 1 is a perspective view of the present invention, wherein the present invention is illustrated in a stowed configuration.

The present invention comprises a barrel 20, a plunger 10, and a deformable tip 30. The barrel 20 defines a generally hollow body of suitable dimensions and material qualities to serve as a momentary storage container to carry a load of medicant 40 into a body cavity. The deformable tip 30 provides a semi-flexible, impermeable exterior surface while being capable of deflecting to permit the passage of the plunger 10 therethrough when fully seated into the barrel 20. The plunger 10 defines a drawable structure configured to be stowed atop the barrel 20 or inserted into the barrel 20 opposite the deformable tip 30 in various stages of use. Accordingly, the deflection of the deformable tip 30 will enable the ejection of the load of medicant 40 ahead of the plunger 10. The barrel 20 and deformable tip 30 will ideally be chemically impermeable to allow for the use of artificial lubricant to aid insertion without compromising the present invention, specifically the elasticity of the deformable tip 30. The barrel 20 is ideally fixed permanently to the deformable tip 30, wherein the seam between the deformable tip 30 and the delivery cylinder 21 has minimal lateral protrusion to prevent patient discomfort to the patient or any intrusion of any bodily fluids to the barrel 20. The present, specifically a stowed configuration of the deformable tip 30 and barrel 20 with plunger 10 as shown in FIG. 1, is contemplated to be packaged as a sterile disposable unit. However, an alternate instance of the present invention may be manufactured for repeated use and sterilization without departing from the original spirit and scope of the present invention.

The plunger 10 further comprises a shaft 11, a head 12, a first flange 13, and at least one first locking mechanism 14. The shaft 11 defines a rigid body capable of fitting within the barrel, terminating in the head 12. The head 12 substantially occupies the inner diameter of the delivery cylinder 21 to enable a user to advance a load of medicant 40 along the delivery cylinder 21 using the shaft 11. The first flange 13 defines a flared structure terminally mounted to the shaft 11 opposite the head 12, providing a suitable platform for a user to exert pressure with their thumb to advance the head 12 along the delivery cylinder 21 and dispense the load of medicant 40. The first locking mechanism 14 is mounted adjacent to the first flange 13, between the first flange 13 and the head 12. Upon full insertion of the plunger 10 into the barrel 20, the first locking mechanism 14 is intended to seize the barrel 20 and fix the plunger 10 and barrel 20 together. This feature will prevent the accidental reuse of an unsterile instance of the present invention, requiring specific and determined effort to unlock and reload the first locking mechanism 14 and barrel 20 after the load of medicant 40 is fully ejected. Further, the first locking mechanism 14 will provide a tactile and auditory 'click' to indicate that the plunger 10 has reached full depth within the barrel 20 and that the load of medicant 40 has been deployed. The barrel 20 further comprises the delivery cylinder 21 and at least one second flange 22. The delivery cylinder 21 defines a hollow tube connecting between the second flange 22 and the deformable tip 30, ideally of uniform interior and exterior diameter. Consequently, the load of medicant 40 may be effectively inserted and advanced along the delivery cylinder 21 without binding to the interior diameter of the delivery cylinder 21. The second flange 22 is terminally connected to the delivery cylinder 21, wherein the second flange 22 protrudes away from the delivery cylinder 21. The first flange 13 is ideally utilized in conjunction with the second flange 22, wherein the second flange 22 is grasped by the user's index and/or middle fingers. The drawing action between the first flange 13 and the second flange 22 should be immediately familiar to most medical professionals, being generally similar to drawing a conventional syringe. The plunger 10 is slidably engaged into the delivery cylinder 21 after the load of medicant 40 has been prepared and inserted into the delivery cylinder 21 so that the plunger 10 may advance the load of medicant 40 into the body cavity. The head 12 slides along the delivery cylinder 21 but will ideally not create a complete seal within the delivery cylinder 21 to prevent injection of volumes of air with the load of medicant 40.

The deformable tip 30 comprises a support ring 31 and a plurality of cuspids 32. The plurality of cuspids 32 is composed of a series of arched, flexible members that may be deformed to enable the dispensation of the load of medicant 40 while simultaneously being capable of collectively maintaining a tapered form against external pressure. Consequently, the plurality of cuspids 32 enable the controlled ejection of the load of medicant 40 while simultaneously providing a suitable penetrating element for most conceivable applications. The support ring 31 is terminally mounted to the delivery cylinder 21, opposite to the second flange 22. Thus, the support ring 31 provides for the seamless transition between the plurality of cuspids 32 and the barrel 20 as previously outlined. The plurality of cuspids 32 defines a set of interlocking members 33 that will collectively form a near-manifold enclosure over the delivery cylinder 21, enclosing and protecting the load of medicant 40 during insertion into a patient. The specific number of members defined within the plurality of cuspids 32, or comprising the set of interlocking members 33, is understood to be as few as two members with no upper limit. However, it is generally considered that a quadricuspid design is suitable for the intended applications described herein.

The plurality of cuspids 32 further comprises an arbitrary cuspid 34 and at least one opposing cuspid 35, wherein the opposing cuspid 35 and the arbitrary cuspid 34 are biased to close relative to each other. In this arrangement the arbitrary cuspid 34 and the opposing cuspid 35 are coterminous, directly abutting one another unless disturbed from within the delivery cylinder 21. More specifically, the arbitrary cuspid 34 and the opposing cuspid 35 are contemplated to present a vaulted structure similar to an intentionally bald arch in an architectural context, i.e. an arch with a missing keystone. The arbitrary cuspid 34 and the opposing cuspid 35 are individually suitably rigid to prevent full collapse of each respecting semi-arch, enabling the plurality of cuspids 32 to compress concentrically during insertion of the deformable tip 30 into a body cavity. Additionally, the arbitrary cuspid 34 comprises at least one first mating surface 36 and the opposing cuspid 35 comprises at least one second mating surface 37, wherein the first mating surface 36 and the second mating surface 37 are forced together by external pressure to form a pseudo-apex of a stable arch, completing the triangulation of the deformable tip 30. This feature protects the load of medicant 40 during insertion while simultaneously providing a flexible, tapered leading element that is understood to cause a minimum of discomfort to a patient. After a suitable position for deployment has been reached, a user may break this temporary support structure by forcing the plunger 10 and the load of medicant 40 outwards through the deformable tip 30 from the inside, deflecting the plurality of cuspids 32 and depositing the load of medicant 40. It is considered that the repeated deflection and closure of the plurality of cuspids 32 during this process may provide a minor tactile feedback to the user as each element of the load of medicant 40 is deposited.

Figure 3:
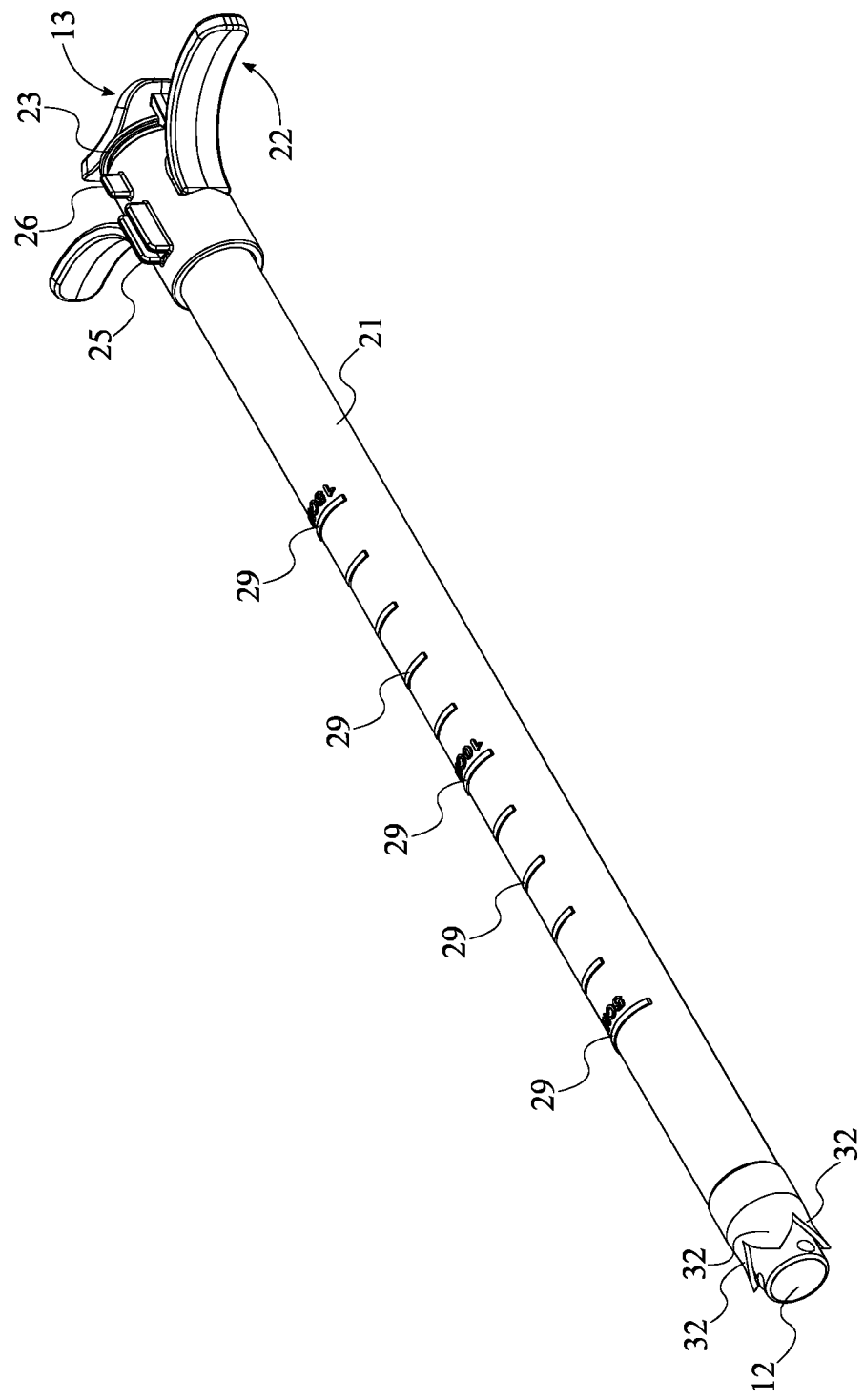
FIG. 3 is a perspective view of the present invention, wherein the present invention is illustrated in a deployed configuration.
Figure 4:
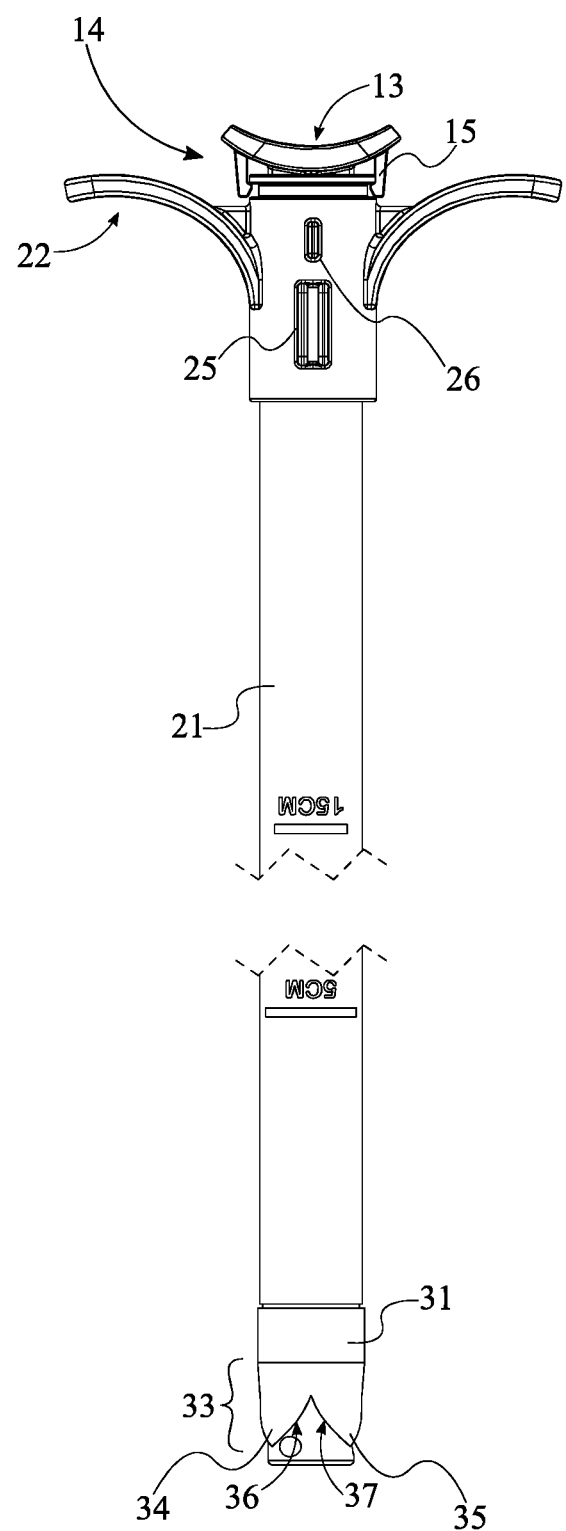
FIG. 4 is a focused top plan view of the present invention, wherein the present invention is illustrated in the deployed configuration.

The first locking mechanism 14 comprises a plurality of latches 15, wherein the plurality of latches 15 protrudes from the first flange 13 towards the shaft 11 of the plunger 10. The barrel 20 additionally comprises an annular ledge 23 terminally mounted to the barrel 20 opposite the deformable tip 30. The plurality of latches 15 defines a series of elongated spars capable of capturing the rearmost end of the barrel 20 and securing to the annular ledge 23 at a predetermined depth as shown in FIG. 4. The annular ledge 23 provides a fixation point about the entirety of the barrel 20, enabling the plurality of latches 15 to engage into the annular ledge 23 regardless of angular orientation. Ideally, the capture position will place the head 12 of the plunger 10 slightly beyond the opposite terminal end of the barrel 20, deforming the plurality of cuspids 32 and ensuring the full ejection of the load of medicant 40 from the delivery cylinder 21 as shown in FIG. 3.

The barrel 20 additionally comprises at least one second locking mechanism 24 mounted adjacent to the second flange 22, between the second flange 22 and the delivery cylinder 21. The second locking mechanism 24 provides a means to fix the plunger 10 externally to the barrel 20 to enable loading of the barrel 20 prior to use. It is contemplated that the second locking mechanism 24 may be utilized to package a medicant dispenser ready for immediate loading and use, truncating the time to delivery of the load of medicant 40. More specifically, the second locking mechanism 24 comprises a jaw 25 and a retainer pin 26 and the plunger 10 further comprises at least one hook 16. The jaw 25 protrudes laterally between the second flange 22 and the delivery cylinder 21 and the retainer pin 26 protrudes from between the second flange 22 and the jaw 25. The hook 16 protrudes laterally from between the first flange 13 and the shaft 11 of the plunger 10 to a distance that the hook 16 may engage into the jaw 25 and be fixed in position by the retainer pin 26. In one instance, the jaw 25 will feature internal ridges to further arrest the movement of the hook 16, while the retainer pin 26 may define a spring element that will actively resist the extraction of the hook 16 from the jaw 25. In another instance, the engagement between the hook 16 and the jaw 25 may be achieved by a frangible connection of the retainer pin 26 to the plunger 10.

Figure 2:
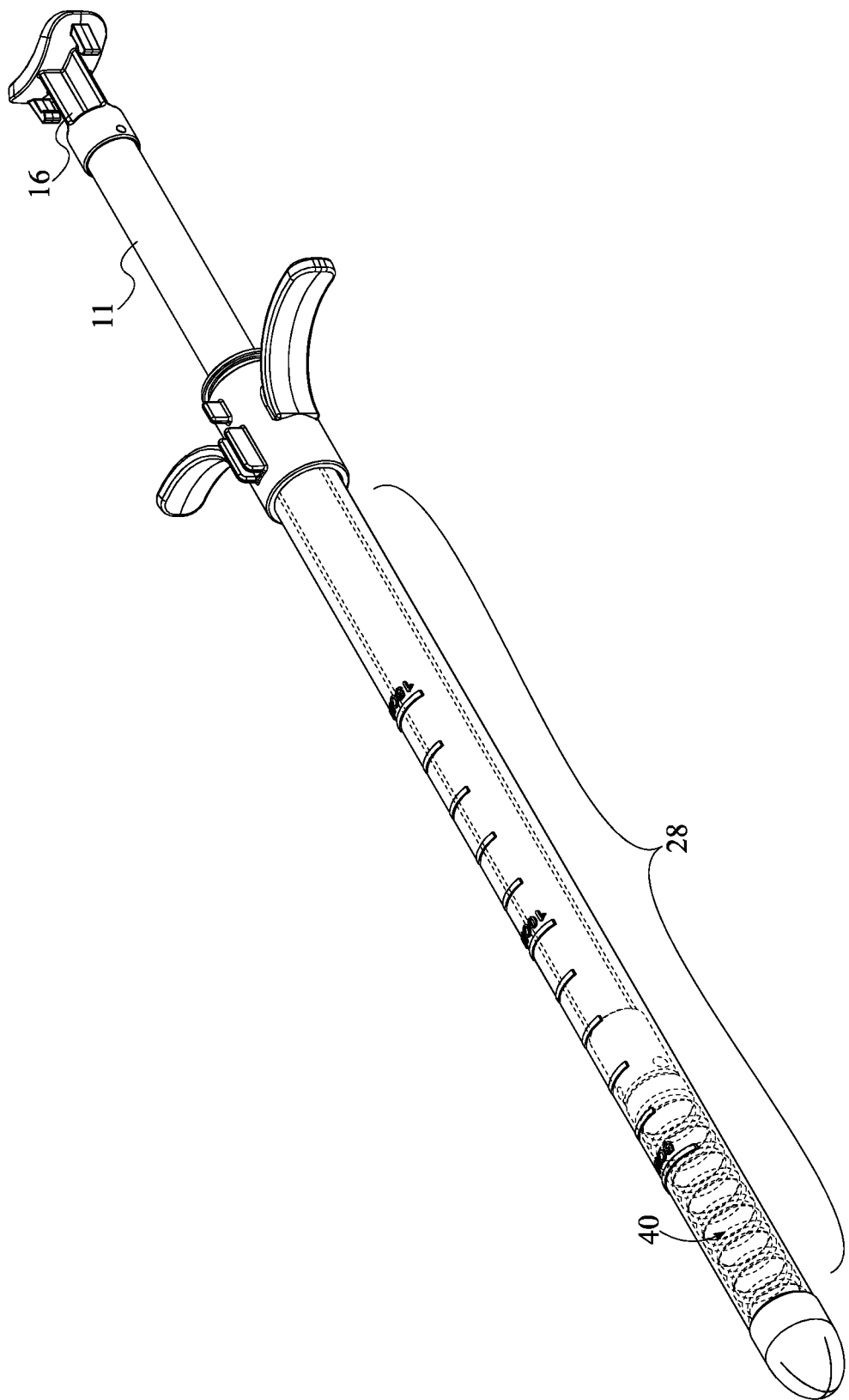
FIG. 2 is a partial-transparent perspective view of the present invention, wherein the present invention is illustrated in a loaded configuration.

It is further considered that, in at least one configuration of the present invention, the delivery cylinder 21 of the barrel 20 comprises an interior chamber 27 extending between the second flange 22 and the support ring 31. The interior chamber 27 is in fluid communication with the deformable tip 30, enabling anything loaded into the interior chamber 27 to be ejected therethrough. The interior chamber 27 is ideally suitable to contain a series of stacked tablets but may be configured to accept pills or items of other types and descriptions without limitation. The interior chamber 27 may be sleeved to adjust the inner diameter or may be manufactured to various geometric profiles without departing from the original scope of the invention. The delivery cylinder 21 additionally comprises at least one transparent section 28, wherein the transparent section 28 extends the length of the delivery cylinder 21 from the second flange 22 to the support ring 31. The material comprising the transparent section 28 extends fully into the interior chamber 27, enabling a user to directly observe the load of medicant 40 contained therein. In the ideal configuration of the medicant dispenser, the delivery cylinder 21 is fully transparent as shown in FIG. 2, enabling the inspection of a prepared load of medicant 40 from any angle. Further, the delivery cylinder 21 may comprise a plurality of visual indicia 29 serially dispersed parallel to the interior chamber 27. Ideally, the plurality of visual indicia 29 will guide a user to both the size of the load of medicant 40 visible through the transparent section 28 and the depth of insertion of the deformable tip 30 and barrel 20 into a patient.

Effective use of the present invention may be achieved in a variety of procedures as may be realized by any reasonably skilled individual in the medical field, but specific consideration is given to the use of the present invention in the obstetric field as a vaginal and rectal applicator of misoprostol. Preparation for use in any case will ideally involve removing the present invention from a sterile casing and loading a desired amount of misoprostol into the interior chamber 27. Then, the plunger 10 may be disengaged from the second locking mechanism 24 and inserted into the barrel 20, seating the head 12 of the plunger 10 against the load of medicant 40. A user may then perform an unguided insertion into the vagina by retracting the labia with one hand, priming the deformable tip 30 and barrel 20 with lubricant and inserting the present invention into the vaginal introitus along the posterior vaginal wall until resistance is met. The present invention should then be withdrawn approximately ten to twenty millimeters to avoid an intracervical insertion of the load of medicant 40. Once in position, the plunger 10 should be pushed until the first locking mechanism 14 produces an audible or tactile alert that the plunger 10 is fully seated and locked into the barrel 20, indicating that the load of medicant 40 has been fully deployed. A user may alternatively guide the present invention to the correct position by placing their fingers into the posterior fornix and slipping the barrel 20 along their knuckles or fingertips until the deformable tip 30 is in deployment position. As previously outlined, the present invention may additionally be used for intrarectal administration be inserting the deformable tip 30 and barrel 20 beyond approximately fifty millimeters and pushing the plunger 10 as previously described. Depth of insertion and quantity of medicant may be measured using the plurality of visual indicia 29 and the transparent section 28 of the delivery cylinder 21, ensuring accurate and appropriate delivery of the load of medicant 40.

Although the invention has been explained in relation to its preferred embodiment, it is to be understood that many other possible modifications and variations can be made without departing from the spirit and scope of the invention as hereinafter claimed.

What is claimed is:

1. A medicant applicator comprising:
    a plunger;
    a barrel;
    a deformable tip;
    the plunger comprising a shaft, a head, a first flange, and at least one first locking mechanism;
    the barrel comprising a delivery cylinder and at least one second flange, wherein the delivery cylinder is configured for receiving a load of a medicant;
    the deformable tip comprising a support ring and a plurality of cuspids;
    the first flange being terminally mounted to the shaft;
    the head being terminally mounted onto the shaft, opposite the first flange;
    the first locking mechanism being mounted adjacent to the first flange;
    the first locking mechanism being positioned in between the first flange and the head;
    the plunger being slidably engaged into the delivery cylinder;
    the second flange being terminally connected to the delivery cylinder;
    the second flange protruding away from the delivery cylinder;
    the support ring being terminally mounted to the delivery cylinder, opposite to the second flange;
    the plurality of cuspids being radially mounted onto the support ring;
    the plurality of cuspids protruding to form a set of interlocking members, wherein the plurality of cuspids is configured for deflecting and closing for dispensing each element of the load of the medicant, and wherein the deflecting and the closing of the plurality of cuspids generates a tactile feedback against an internal wall for a body cavity of a user advancing the load of the medicant along the delivery cylinder using the shaft;
    the delivery cylinder comprising an interior chamber;
    the interior chamber extending between the second flange and the support ring; and
    the interior chamber being in fluid communication with the deformable tip, wherein the interior chamber comprises a sleeve, and wherein the sleeve is telescopically engaged within the interior chamber to reduce an inner receiving diameter of the interior chamber, and wherein the sleeve extends a length of the interior chamber.

2. The medicant applicator as claimed in claim 1 comprising:
    the plurality of cuspids further comprising an arbitrary cuspid and at least one opposing cuspid;
    the opposing cuspid and the adjacent cuspid being biased to close relative to each other; and
    the arbitrary cuspid and the opposing cuspid being coterminous.

3. The medicant applicator as claimed in claim 2 comprising:
    the arbitrary cuspid further comprising at least one first mating surface;

the opposing cuspid further comprising at least one second mating surface; and
the plurality of cuspids being responsive to external pressure, the first mating surface and the second mating surface collapsing together to provide mutual support.

4. The medicant applicator as claimed in claim 1 comprising:
the first locking mechanism comprising a plurality of latches;
the barrel further comprising an annular ledge;
the plurality of latches protruding from the first flange, towards the shaft;
the annular ledge being terminally mounted to the barrel, opposite the deformable tip;
the second flange being positioned in between the annular ledge and the deformable tip;
the second flange being positioned offset from the annular ledge; and
the plurality of latches being configured for engaging the annular ledge, wherein the engaging of the plurality of latches to the annular ledge generates an auditory feedback after dispensing the load of medicant.

5. The medicant applicator as claimed in claim 1 comprising:
the barrel further comprising at least one second locking mechanism;
the second locking mechanism being mounted adjacent to the second flange; and
the second locking mechanism being positioned between the second flange and the delivery cylinder.

6. The medicant applicator as claimed in claim 5 comprising:
the second locking mechanism comprising a jaw and a retainer pin;
the plunger further comprising at least one hook;
the second flange comprising an index-finger grip and a middle-finger grip;
the jaw protruding laterally between the second flange and the delivery cylinder;
the retainer pin being positioned between the second flange and the jaw;
the hook protruding laterally from between the first flange and the shaft;
the hook being configured to engage into the jaw, wherein the movement of the plunger is arrested by the retainer pin while the hook is engaged into the jaw;
the index-finger grip and the middle-finger grip being positioned opposite to each other about the delivery cylinder;
the jaw and the retainer pin being positioned in between the index-finger grip and the middle-finger grip about the delivery cylinder; and
the jaw and the retainer pin being positioned offset from each other along an axial length of the delivery cylinder.

7. The medicant dispenser as claimed in claim 1 comprising:
the delivery cylinder further comprising at least one transparent section;
the transparent section extending between the second flange and the support ring; and
the transparent section traversing normally into the interior chamber.

8. The medicant dispenser as claimed in claim 1 comprising:
the delivery cylinder further comprising a plurality of visual indicia; and
the plurality of visual indicia being serially dispersed parallel to the interior chamber between the second flange and the support ring, wherein the plurality of visual indicia is configured to guide the user regarding a depth of insertion of the deformable tip and the barrel into a body cavity.

9. A medicant applicator comprising:
a plunger;
a barrel;
a deformable tip;
the plunger comprising a shaft, a head, a first flange, and at least one first locking mechanism;
the barrel comprising a delivery cylinder and at least one second flange, wherein the delivery cylinder is configured for receiving a load of a medicant;
the deformable tip comprising a support ring and a plurality of cuspids;
the plurality of cuspids further comprising an arbitrary cuspid and at least one opposing cuspid;
the first flange being terminally mounted to the shaft;
the head being terminally mounted onto the shaft, opposite the first flange;
the first locking mechanism being mounted adjacent to the first flange;
the first locking mechanism being positioned in between the first flange and the head;
the plunger being slidably engaged into the delivery cylinder;
the second flange being terminally connected to the delivery cylinder;
the second flange protruding away from the delivery cylinder;
the support ring being terminally mounted to the delivery cylinder, opposite to the second flange;
the plurality of cuspids radially mounted onto the support ring;
the plurality of cuspids protruding to form a set of interlocking members;
the opposing cuspid and the adjacent cuspid being biased to close relative to each other;
the arbitrary cuspid and the opposing cuspid being coterminous, wherein the plurality of cuspids is configured for deflecting and closing for dispensing each element of the load of the medicant, and wherein the deflecting and the closing of the plurality of cuspids generates a tactile feedback against an internal wall for a body cavity of a user advancing the load of the medicant along the delivery cylinder using the shaft;
the first locking mechanism comprising a plurality of latches;
the barrel further comprising an annular ledge;
the plurality of latches protruding from the first flange, towards the shaft;
the annular ledge being terminally mounted to the barrel, opposite the deformable tip;
the second flange being positioned in between the annular ledge and the deformable tip;
the second flange being positioned offset from the annular ledge;
the plurality of latches being configured for engaging the annular ledge, wherein the engaging of the plurality of latches to the annular ledge generates an auditory feedback after dispensing the load of medicant;
the barrel further comprising at least one second locking mechanism;
the second locking mechanism being mounted adjacent to the second flange;

the second locking mechanism being positioned between the second flange and the delivery cylinder;

the second locking mechanism comprising a jaw and a retainer pin;

the plunger further comprising at least one hook;

the second flange comprising an index-finger grip and a middle-finger grip;

the jaw protruding laterally between the second flange and the delivery cylinder;

the retainer pin being positioned between the second flange and the jaw;

the hook protruding laterally from between the first flange and the shaft the hook being configured to engage into the jaw, wherein the movement of the plunger is arrested by the retainer pin while the hook is engaged into the jaw;

the index-finger grip and the middle-finger grip being positioned opposite to each other about the delivery cylinder;

the jaw and the retainer pin being positioned in between the index-finger grip and the middle-finger grip about the delivery cylinder; and the jaw and the retainer pin being positioned offset from each other along an axial length of the delivery cylinder.

10. The medicant applicator as claimed in claim 9 comprising:

the arbitrary cuspid further comprising at least one first mating surface;

the opposing cuspid further comprising at least one second mating surface; and the plurality of cuspids being responsive to external pressure, the first mating surface and the second mating surface collapsing together to provide mutual support.

11. The medicant dispenser as claimed in claim 9 comprising:

the delivery cylinder comprising an interior chamber;

the interior chamber extending between the second flange and the support ring; and the interior chamber being in fluid communication with the deformable tip, wherein the interior chamber comprises a sleeve, and wherein the sleeve is telescopically engaged within the interior chamber to reduce an inner receiving diameter of the interior chamber, and wherein the sleeve extends a length of the interior chamber.

12. The medicant dispenser as claimed in claim 11 comprising:

the delivery cylinder further comprising at least one transparent section;

the transparent section extending between the second flange and the support ring; and the transparent section traversing normally into the interior chamber.

13. The medicant dispenser as claimed in claim 11 comprising:

the delivery cylinder further comprising a plurality of visual indicia; and the plurality of visual indicia being serially dispersed parallel to the interior chamber between the second flange and the support ring, wherein the plurality of visual indicia is configured to guide the user regarding a depth of insertion of the deformable tip and the barrel into a body cavity.

* * * * *